United States Patent
Moszner et al.

(10) Patent No.: US 8,466,212 B2
(45) Date of Patent: Jun. 18, 2013

(54) PROCESS FOR PREPARING DENTAL MATERIALS HAVING LOW POLYMERIZATION SHRINKAGE

(75) Inventors: Norbert Moszner, Triesen (LI); Helmut Ritter, Wuppertal (DE); Urs-Karl Fischer, Arbon (CH); Monir Tabatabai, Düsseldorf (DE); Matthias Schaub, Linsengericht (DE); Andreas Utterodt, Neu-Anspach (DE)

(73) Assignees: Ivoclar Vivadent AG, Schaan (LI); Haraeus Kulzer GmbH, Hanau (DE)

( * ) Notice: Subject to any disclaimer, the term of this patent is extended or adjusted under 35 U.S.C. 154(b) by 0 days.

(21) Appl. No.: 12/859,052

(22) Filed: Aug. 18, 2010

(65) Prior Publication Data

US 2010/0311863 A1    Dec. 9, 2010

Related U.S. Application Data

(62) Division of application No. 11/897,228, filed on Aug. 29, 2007, now abandoned.

(30) Foreign Application Priority Data

Aug. 29, 2006 (DE) .......................... 10 2006 040 439
Jul. 30, 2007 (DE) .......................... 10 2007 035 734

(51) Int. Cl.
*A61K 6/083* (2006.01)
*A61C 5/00* (2006.01)

(52) U.S. Cl.
USPC ........................ 523/116; 433/228.1; 106/35

(58) Field of Classification Search
USPC ........................................ 523/116; 433/228.1
See application file for complete search history.

(56) References Cited

U.S. PATENT DOCUMENTS 3,663,501 A * 5/1972 Adams .......................... 523/203
4,866,198 A * 9/1989 Harris ............................. 560/61

OTHER PUBLICATIONS http://en.wikipeida.org/wiki/Calixarene, Mar. 16, 2012.

* cited by examiner

*Primary Examiner* — Tae H Yoon
(74) *Attorney, Agent, or Firm* — Ann M. Knab; Thad McMurray

(57) ABSTRACT

The present invention relates to dental materials composed of calix[n]arenes and also to the use thereof for cements, composites, adhesives and coating materials in the dental field. The materials include (a) 0.5 to 90% by weight of at least one polymerizable calix[n]arene according to formula (I),
(b) 0.01 to 5% by weight of initiator,
(c) 0 to 90% by weight of at least one additional monomer which can polymerize under cationic and/or radical conditions and/or which can polymerize by ring opening,
(d) 0 to 85% by weight of filler,
(e) 0.01 to 5% by weight of additive and
(f) 0 to 70% by weight of solvent.

16 Claims, No Drawings

PROCESS FOR PREPARING DENTAL MATERIALS HAVING LOW POLYMERIZATION SHRINKAGE

CROSS-REFERENCE TO RELATED APPLICATIONS

This application is a Divisional Application of U.S. patent application Ser. No. 11/897,228, filed Aug. 29, 2007 now abandoned, which claims priority from DE 10 2006 040 439.4 filed Aug. 29, 2006, and DE 10 2007 035 734.8 filed Jul. 30, 2007, the contents of all of which are incorporated herein by reference.

BACKGROUND OF THE INVENTION

1. Field of the Invention

The present invention relates to dental materials comprising calix[n]arenes having low polymerization shrinkage and comparable mechanical properties.

2. Description of the Related Art

Calix[n]arenes are cyclic oligomers, known as $1_n$-metacyclophanes (Scheme 1, formula 1), which are accessible by condensation of p-alkylphenols with formaldehyde (Scheme 1, formula 2) or of resorcinol with aldehydes (Scheme 1, formula 3), the phenolic OH groups being arranged in the endo (intraannular) or exo (extraannular) position. In this connection, the particular bowl- or cup-like conformation of the calix[n]arenes has resulted in numerous applications in catalysis, chromatography, analysis or sensor technology (V. Böhmer, Angew. Chem., 107 (1995), 785-818).

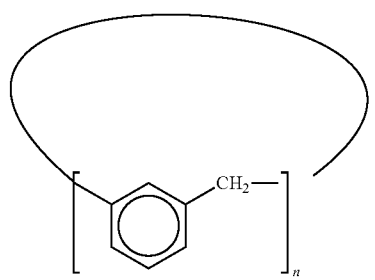

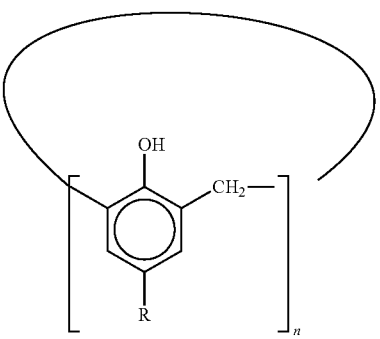

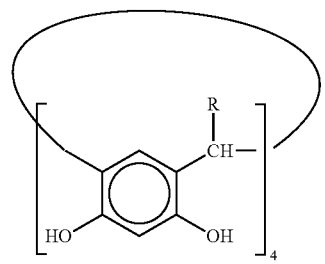

Scheme 1: 1: $1_n$-metacyclophanes, 2: calix[n]arene of a p-substituted phenol and 3: calix[4]resorcarene Quite a number of papers on the synthesis and polymerization of polymerizable calix[n]arenes are known from the scientific literature. Examples of this are the synthesis of the radically polymerizable 5-[3-(methacryloyloxy)propyl]-25,26,27,28-tetrabutoxycalix[4]arene (D. M. Gravett and J. E. Guillet, Macromolecules, 29 (1996), 617-724) or of 5-(1-(acryloyloxypropyloxymethyl)-25,26,27,28-tetra(2-ethoxyethyl)calix[4]arene (M. T. Blanda and E. Adou, Polymer, 39 (1998), 3821-3826), the synthesis and radical polymerization of p-alkylcalix[6]arenes having (meth)acryl groups, such as, e.g., the hexa(meth)acrylates of p-methyl- or p-tert-butylcalix [6]arene, (M. Iyo, K. Tsutsui, A. Kameyama and T. Nishikubo, J. Polym. Sci., Part A: Polym. Chem., 37 (1999), 3071-3078) or the synthesis of cationically polymerizable calix[n]arenes, such as, e.g., of 5,11,17,23,29,35-hexamethyl-37,38,39,40,41,42-hexakis(allyloxy)calix[6]arene (T. Nishikubo, A. Kameyama, K. Tsutsui and M. Iyo, J. Polym. Sci., Part A: Polym. Chem., 37 (1999), 1805-1814).

The use of calix[n]arenes in combination with polymerizable formulations is known from the patent literature. Thus, e.g., U.S. Pat. No. 4,636,539, U.S. Pat. No. 4,718,966, U.S. Pat. No. 4,912,183, EP 235 935 and FR 2 795 077 describe the use of calix[n]arenes, not modified reactively, as accelerators for cyanoacrylate adhesives.

U.S. Pat. No. 4,699,966 describes calix[n]arenes functionalized with acrylate or methacrylate groups and polymers thereof as sequestering agents for metal ions. Additional, more specific, polymerizable calix[n]arene and oxacalixarene derivatives with at least one phenolic side group are described in U.S. Pat. No. 5,216,185.

JP 09-263560 describes calix[n]arene derivatives which are functionalized with (meth)acrylate, vinyl or propenyl groups and can be polymerized thermally or photochemically. JP 11-043524 describes similar systems which, however, are additionally modified with polyalkylene oxide groups.

WO 2005/075398 A1 and JP 2002-088007 describe polymerizable calix[n]arene derivatives which result, in curable photoresists, in an improved resistance to heat. JP 2004-137395 claims a cellulose acrylate film comprising a polymerizable calix[n]arene derivative with the advantage of improved mechanical and optical properties.

JP 2002-003563 and JP 09-263560 describe calix[n]arene derivatives comprising polymerizable groups (acrylate, methacrylate, vinyl, vinyl ether, and the like) and acid or anhydride groups. These find use as etching resists, adhesives, lacquers or coatings.

GB 2 185 261 describes a radically polymerizable composition as adhesive filler comprising a calix[n]arene derivative. JP 02-124850 describes the preparation of calix[n]arene derivatives by heating p-tert-butylcalix[6]arenes with glycidyl methacrylate and tri(n-butyl)amine. U.S. Pat. No. 4,617,336 and CA 1 273 954 describe calixarenes with acrylate groups for the stabilizing of organic materials, in particular polymers.

JP 2000-256362 describes polymerizable calix[n]arene derivatives which are functionalized with spiroorthoester groups. These compounds, which are distinguished by a polymerization without shrinkage in volume, are suitable, inter alia, for use as coating materials.

JP 2000-264953 describes, finally, curable epoxy resins which acquire advantageous properties by addition of calix[n]arenes, such as a high crosslinking density, high resistance to heat and good mechanical properties.

WO 2005/120229 describes substances which release terpenes and/or aromatic alcohols. The substances and compositions depicted can, inter alia, also comprise calix[n]arenes and are used, first and foremost, to prevent microorganisms from adhering to surfaces. By way of example, compositions are described which prevent the development of microorganisms in jointing compounds. Likewise, the use of compositions comprising calix[n]arene for the cleaning of prostheses is described.

U.S. Pat. No. 4,699,966 describes calix[n]arenes and polymers prepared therefrom, the calix[n]arenes being mixed with an initiator and polymerized using light. The use as filler-comprising dental material or as component in such materials is not described.

U.S. Pat. No. 6,117,944 A describes the preparation and the determination of the reactivity of various calixarene-comprising filler-free compositions. The use in dental materials is not a subject-matter of this patent application.

EP 1 712 537 A1 describes a multitude of different calix[n]arenes in different compositions. These, though, comprise no filler and no additional radically polymerizable components.

EP 432 990 A2 describes filler-free compositions for the masking and coating of metals. The materials are cured from a solution using actinic radiation. Filler-comprising dental materials with calix[n]arene are not disclosed.

EP 196 895 B1 describes filler-free adhesive compositions which contain no filler. The polymers produced comprise calix[n] arene sequences.

WO 2005/056741 A1 describes non-stick compositions. These are devoid of filler and have, as coating, even for prostheses and dental or oral care products, no direct reference to dental materials, which concern materials for the preservation or reconstruction of the masticatory apparatus. Filler-comprising compositions for dental use are not disclosed.

WO 94/15907 A1 describes calix[n]arenes comprising cyano groups which are used devoid of filler and for which a slight shrinkage was observed. Filler-comprising dental materials are not disclosed.

SUMMARY OF THE INVENTION

Therefore, it is the object of the invention to make available dental materials which, in comparison with the conventional materials based on normal methacrylates, are distinguished by a lower polymerization shrinkage and good mechanical properties and, in addition, allow additional advantageous properties, such as, e.g., self-adhesion, to be obtained.

This object is achieved by dental materials which exhibit the following components or are composed of the following components:

(a) 0.5 to 90% by weight, particularly preferably 0.5 to 40% by weight, of at least one polymerizable calix[n]arene according to formula (I),
(b) 0.01 to 5% by weight, particularly preferably 0.01 to 20 by weight, of initiator,
(c) 0 to 90% by weight, particularly preferably 1 to 70% by weight, of at least one additional monomer which can polymerize under cationic and/or radical conditions and/or at least one additional monomer which can polymerize by ring opening, (meth)acrylates which can polymerize by ring opening or polyfunctional (meth)acrylates being preferred,
(d) 0 to 85% by weight, particularly preferably 3 to 80% by weight, of filler and
(e) 0.01 to 5% by weight, particularly preferably 0.01 to 3% by weight, of additive,
the percentages each time adding up to 100%.

The various features of novelty which characterize the invention are pointed out with particularity in the claims annexed to and forming a part of the disclosure. For a better understanding of the invention, its operating advantages, specific objects attained by its use, reference should be had to, descriptive matter in which there are described preferred embodiments of the invention.

DETAILED DESCRIPTION OF THE INVENTION

Use is preferably made, according to the invention, of calix[n]arenes of the general formula (I):

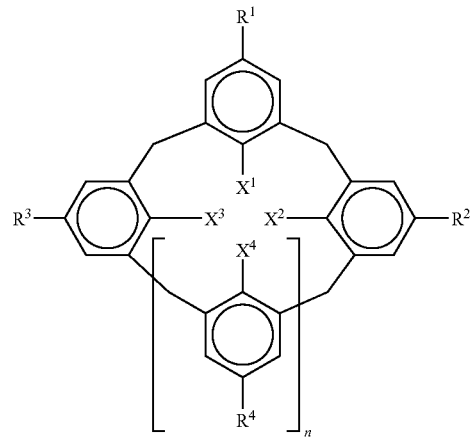

in which
n=1 to 5,
$R^1$-$R^4$=independently of one another, H, a $C_1$- to $C_{15}$-alkyl radical which can be interrupted by O, a phenyl radical or a benzyl radical,
$X^1$ represents a group with the structure:
$Y^1$—$R_a^1(Y_a^1R_b^1$-$PG^1)_m$, in which
$Y^1$=not present or O, ester, amide or urethane,
$R_a^1$=an m-valent organic radical which can comprise from 1 to 30 carbon atoms and, if appropriate, also from 0 to 6 heteroatoms, such as O, S or N,
m=1 to 3,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group, e.g. a group which can polymerize under radical conditions, such as (meth)acrylate, (meth)acrylamide, vinyl, allyl or styryl; a cyclic group which can polymerize under radical conditions by ring opening, such as, e.g., the groups

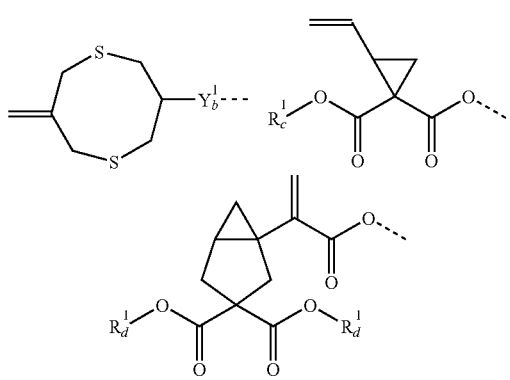

or a group which can polymerize under cationic conditions, such as, e.g., a vinyl ether or glycidyl group, a cycloaliphatic epoxide or oxetane group or a polymerizable nitrone group, with $Y_b^1$=not present or O, ester, amide or urethane, $R_c^1$, $R_d^1$=independently of one another, $C_1$- to $C_{15}$-alkyl radical which can be interrupted by O, a phenyl radical or a benzyl radical;

and with furthermore $X^2$-$X^4$=independently of one another, not present, OH or $C_1$- to $C_{10}$-alkyl radical and which can have, independently of one another, the same meaning of $X^1$ and, in addition, can represent a group with the structure: $(Y_a^2\!-\!R_b^2\text{-AG})_p$, in which $Y_a^2$=not present or, if appropriate, O, ester, amide or urethane, $R_b^2$=a p-valent organic radical which can comprise from 1 to 20 carbon atoms and, if appropriate, also from 0 to 4 heteroatoms, such as O or N, p=1 to 3 and AG=an anchoring group, such as, e.g., —P=O(OH)$_2$, —O—P=O(OH)$_2$, —COON or —O—SO$_2$OH.

Particular preference is given to polymerizable calix[n]arenes corresponding to the general formula (I) in which the variables of the groups indicated above have the following meanings, it being possible for these meanings to be chosen independently of one another:

n=1 to 3, $R^1$-$R^4$=independently of one another, H, a $C_1$- to $C_{10}$-alkyl radical which can be interrupted by O, or a benzyl radical, $X^1$ represents a group with the structure:

$Y^1\!-\!R_a^1(Y_a^1\!-\!R_b^1\text{-PG}^1)_m$, in which $Y^1$=not present or O or ester, $R_a^1$=an m-valent organic radical which can comprise from 1 to 15 carbon atoms and, if appropriate, also from 0 to 3 oxygen atoms, m=1 to 2, $Y_a^1$=not present or O or ester, $R_b^1$=not present or a $C_1$-$C_{16}$-alkylene radical which can be interrupted by oxygen atoms, $PG^1$=a polymerizable group, e.g., a group which can polymerize under radical conditions, such as (meth)acrylate or (meth)acrylamide, a cyclic group which can polymerize under radical conditions by ring opening, such as, e.g., the groups

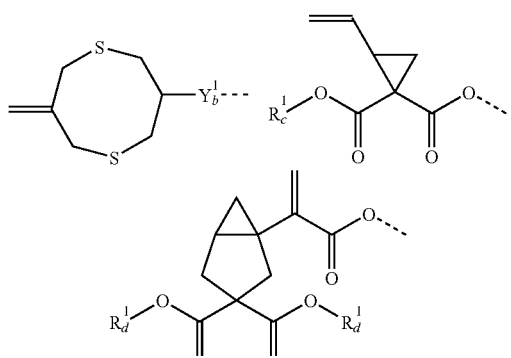

or a group which can polymerize under cationic conditions, such as, e.g., a cycloaliphatic epoxide or oxetane group or a polymerizable nitrone group, with $Y_b^1$=not present or O, ester or urethane, $R_c^1$, $R_d^1$=independently of one another, $C_1$- to $C_5$-alkyl radical, a phenyl radical or a benzyl radical; and with furthermore $X^2$-$X^4$=independently of one another, not present or $C_1$- to $C_{10}$-alkyl radical and which can have, independently of one another, the same meaning of $X^1$ and, in addition, can represent a group with the structure: $(Y_a^2\!-\!R_b^2\text{-AG})_p$, in which $Y_a^2$=not present or O or ester, $R_b^2$=a p-valent organic radical which can comprise from 1 to 10 carbon atoms and, if appropriate, also from 0 to 2 oxygen atoms, p=1 to 2 and AG=an anchoring group, such as, e.g., —P=O(OH)$_2$, —O—P=O(OH)$_2$, —COOH or —O—SO$_2$OH.

The calix[n]arenes of the general formula (I) used according to the invention can be obtained, starting from suitably functionalized calix[n]arenes, by reaction with appropriate polymerizable compounds comprising acid groups. Thus, e.g., homogeneously substituted polymerizable calix[n]arenes can be prepared by modifying HO-functionalized calix[n]arenes with methacryloyl chloride:

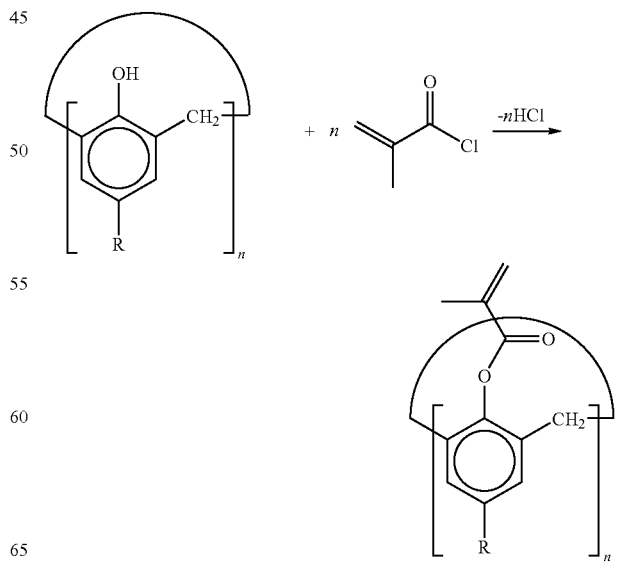

A concrete example is the preparation of the hexamethacrylate of p-tert-butylcalix[6]arene:

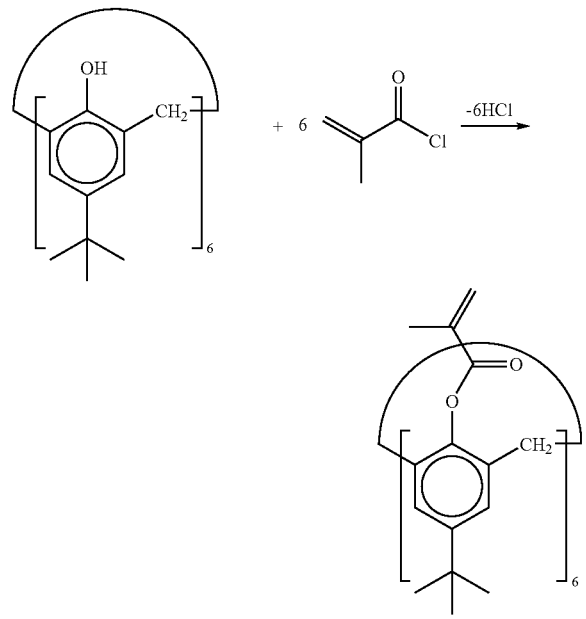

Nonhomogeneously substituted polymerizable calix[n]arenes can be analogously prepared by modifying HO-functionalized calix[n]arenes with mixtures of polymerizable acid chlorides, such as e.g., methacryloyl and acryloyl chloride. Furthermore, polymerizable calix[n]arenes carrying additional acid groups can be synthesized by sequential reaction, e.g. polymerizable calix[n]arenes with dihydrogenphosphate groups by partial reaction with methylacryloyl chloride, followed by phosphorylation with phosphoryl chloride.

Suitable functionalized calix[n]arenes for the synthesis of the polymerizable calix[n]arenes according to the invention corresponding to the general formula (I) are known from the literature; a survey thereof can be found in the review by V. Böhmer (Angew. Chem., 107 (1995), 785-818). In accordance with this, a distinction is made between, on the one hand, one-pot processes, in which, e.g., tert-butylphenol is reacted with formaldehyde under alkaline conditions, depending on the temperature and the amount of base, to give the tetra-, hexa- or octamer. On the other hand, differently substituted calixarenes can be synthesized stepwise by alternating hydroxymethylation and condensation steps and, finally, subsequent cyclization of the linear oligomers thus obtained.

Suitable functionalized cyclic monomers for the synthesis of calix[n]arenes of the general formula (I) which can polymerize under radical conditions by ring opening are known from the literature. For example, the synthesis of vinylcyclopropanes and of bicyclic cyclopropylacrylates is described by N. Moszner et al., Macromol. Rapid. Commun., 18 (1997), 775-780, or A. de Meijere et al., Eur. J. Org. Chem., 2004, 3669-3678. The synthesis of functionalized cyclic allyl sulphides has been published by R. A. Evans and E. Rizzardo in J. Polym. Sci., Part A. Polym. Chem., 39 (2001), 202-215; Macromolecules, 33 (2000), 6722-6731.

The calix[n]arenes corresponding to the general formula (I) which can polymerize under radical conditions used according to the invention allow the preparation of dental materials which, in comparison with the conventional materials based on normal dimethacrylates, are distinguished by a lower polymerization shrinkage and good mechanical properties and, in addition, it is possible, e.g. by the use of calix[n]arenes corresponding to the general formula (I) which can polymerize under radical conditions and which comprise acid groups, to obtain additional properties, such as, e.g., self-adhesion.

Accordingly, the materials according to the invention find use as self-adhesive dental materials, e.g. filling composites, cements and coating materials. Likewise, the dental materials according to the invention can be used as adhesives.

Even if the use of the compositions according to the invention is focused on the use in the dental field, these materials have a broad range of uses, e.g. they can be used as protective and masking lacquers for optics, electronics and the motor vehicle industry.

The calix[n]arenes corresponding to the general formula (I) which can polymerize under radical conditions used according to the invention can be used in a mixture with conventional monomers which can polymerize under radical conditions, in particular with difunctional (meth)acrylate crosslinking agents. Suitable with regard to this are in particular crosslinking di- or polyfunctional acrylates or methacrylates, such as, e.g., bisphenol A di(meth)acrylate, Bis-GMA (an addition product of methacrylic acid and bisphenol A diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythrityl tetra(meth)acrylate, and 1,4-butanediol di(meth)acrylate, 1,10-decanediol di(meth)acrylate or 1,12-dodecanediol di(meth)acrylate.

Particularly advantageous is the use of the calix[n]arenes corresponding to the general formula (I) which can polymerize under radical conditions in a mixture with known monomers which can polymerize under radical conditions by ring opening with little shrinkage, such as, e.g., mono- or polyfunctional vinylcyclopropanes or bicyclic cyclopropaneacrylate derivatives (cf. DE 196 16 183 C2 or EP 03 022 855) or cyclic allyl sulphides (cf. U.S. Pat. No. 6,043,361 or U.S. Pat. No. 6,344,556), which, in addition, can also be used in combination with the di(meth)acrylate crosslinking agents listed above. Preferred monomers which can polymerize by ring opening are such vinylcyclopropanes as 1,1-di(ethoxycarbonyl)- or 1,1-di(methoxycarbonyl)-2-vinylcyclopropane or the esters of 1-ethoxycarbonyl- or 1-methoxycarbonyl-2-vinylcyclopropanecarboxylic acid with ethylene glycol, 1,1,1-trimethylolpropane, 1,4-cyclohexanediol or resorcinol. Preferred bicyclic cyclopropane derivatives are 2-(bicyclo[3.1.0]hex-1-yl)acrylic acid methyl or ethyl ester or the disubstitution products in the 3 position thereof, such as (3,3-bis(ethoxycarbonyl)bicyclo[3.1.0]hex-1-yl)acrylic acid methyl or ethyl ester. Preferred cyclic allyl sulphides are in particular the addition products of 2-(hydroxymethyl)-6-methylene-1,4-dithiepane or 7-hydroxy-3-methylene-1,5-dithiacyclooctane with 2,2,4-trimethylhexamethylene 1,6-diisocyanate or the asymmetric hexamethylene diisocyanate trimer Desmodur® VP LS 2294 from Bayer AG.

Particularly suitable is the use of the calix[n]arenes corresponding to the general formula (I) which can polymerize under cationic conditions according to the invention in a mixture with known monomers which can polymerize under cationic conditions by ring opening with low shrinkage, such as, e.g., glycidyl ethers or cycloaliphatic epoxides, cyclic ketene acetals, spiroorthocarbonates, oxetanes or bicyclic orthoesters. Examples are: 2-methylene-1,4,6-trioxaspiro[2.2]nonane, 3,9-dimethylene-1,5,7,11-tetraoxaspiro[5.5]

undecane, 2-methylene-1,3-dioxepane, 2-phenyl-4-methylene-1,3-dioxolane, bisphenol A diglycidyl ether, 3,4-epoxycyclohexylmethyl 3,4-epoxycyclohexanecarboxylate, bis(3,4-epoxycyclohexylmethyl) adipate, vinylcyclohexane dioxide, 3-ethyl-3-(hydroxymethyl)oxetane, 1,10-decanediylbis(oxymethylene)bis(3-ethyloxetane) or 3,3-(4-xylylenedioxy)bis(methyl-3-ethyloxetane) or additional epoxides mentioned in EP 0 879 257 B1. Silica polycondensates, which can be obtained, for example, by hydrolytic condensation of silanes carrying groups which can polymerize under cationic conditions, preferably, e.g., epoxide, oxetane or spiroorthoester groups, are also suitable as matrix systems which can polymerize under cationic conditions. Such silica polycondensates are described, for example, in DE 41 33 494 C2 or U.S. Pat. No. 6,096,903.

The dental materials according to the invention based on the calix[n]arenes corresponding to the general formula (I) which can polymerize under radical conditions can be polymerized using the known radical initiators (cf. Encyclopaedia of Polymer Science and Engineering, Vol. 13, Wiley-Intersci. Pub., New York, etc., 1988, 754ff.). Photoinitiators (cf. J. P. Fouassier and J. F. Rabek (Ed.), Radiation Curing in Polymer Science and Technology, Vol. II, Elsevier Applied Science, London and New York, 1993) for the UV or visible region, such as, e.g.: benzoin ethers, dialkyl benzil ketals, dialkoxyacetophenones, acyl- or bisacylphosphine oxides, or α-diketones, such as 9,10-phenanthrenequinone, diacetyl, furil, anisil, 4,4'-dichlorobenzil and 4,4'-dialkoxybenzil and camphorquinone, are particularly suitable.

Furthermore, azo compounds, such as 2,2'-azobis(isobutyronitrile) (AIBN) or azobis(4-cyanovaleric acid), or peroxides, such as dibenzoyl peroxide, dilauroyl peroxide, tert-butyl peroctoate, tert-butyl perbenzoate or di(tert-butyl) peroxide, can also be used. Benzopinacol and 2,2'-dialkylbenzopinacols are suitable as initiators for heat curing.

Combinations with aromatic amines are also frequently preferred in order to accelerate the initiation using peroxides or α-diketones. Redox systems which have already proven to be worthwhile are: combinations of benzoyl peroxide or camphorquinone with amines, such as N,N-dimethyl-p-toluidene, N,N-di(hydroxyethyl)-p-toluidene, ethyl p-(dimethylamino)benzoate or structurally related systems. In addition, redox systems consisting of peroxides and such reducing agents as, e.g., ascorbic acid, barbiturates or sulphinic acids are also suitable.

The dental materials according to the invention based on the calix[n]arenes corresponding to the general formula (I) which can polymerize under cationic conditions can be cured with the known cationic photoinitiators, in particular with diaryliodonium or triarylsulphonium salts, if appropriate in the presence of suitable sensitizers, such as, e.g., camphorquinone. Examples of suitable diaryliodonium salts which can be used in the visible region with camphorquinone or thioxanthones as sensitizer are the commercially accessible (4-octyloxyphenyl)phenyliodonium hexafluoroantimonate or (isopropylphenyl)(methylphenyl)iodonium tetrakis(pentafluorophenyl)borate.

In addition, the dental materials according to the invention based on the polymerizable calix[n]arenes can comprise one or more fillers, preferably organic or inorganic particulate fillers. Preferred inorganic particulate fillers are amorphous spherical nanoparticulate fillers based on oxides, such as pyrogenic silica or precipitated silica, $ZrO_2$ and $TiO_2$ or mixed oxides of $SiO_2$, $ZrO_2$ and/or $TiO_2$ with a mean particle size of 10 to 200 nm, minifillers, such as quartz, glass ceramic or glass powders with a mean particle size of 0.2 to 5 μm, and also fillers which are opaque to X-rays, such as ytterbium trifluoride or nanoparticulate tantalum(V) oxide or barium sulphate. In addition, fibrous fillers, such as glass fibres, polyamide fibres or carbon fibres, can also be used.

Finally, additional additives, such as, e.g., stabilizers, UV absorbers, dyes or pigments, and also solvents, such as, e.g., water, ethanol, acetone or ethyl acetate, or lubricants, can, if required, be added to the dental materials according to the invention based on the polymerizable calix[n]arenes.

In this connection, the dental materials according to the invention are composed, depending on the intended purpose, preferably of the following components:

Cements according to the invention preferably comprise:
(a) 0.5 to 30% by weight, particularly preferably 0.5 to 20% by weight, of at least one polymerizable calix[n]arene according to formula (I),
(b) 0.01 to 2% by weight, particularly preferably 0.01 to 1.5% by weight, of initiator,
(c) 1 to 30% by weight, particularly preferably 5 to 20% by weight, of at least one additional monomer which can polymerize under cationic and/or radical conditions and/or one additional monomer which can polymerize by ring opening, preferably a polyfunctional (meth)acrylate,
(d) 5 to 70% by weight, particularly preferably 10 to 60% by weight, of filler and
(e) 0.01 to 5% by weight, preferably 0.01 to 2% by weight, particularly preferably 0.01 to 1% by weight, of additive,
the percentages each time adding up to 100%.

Filling composites according to the invention preferably comprise:
(a) 0.5 to 30% by weight, particularly preferably 0.5 to 20% by weight, of at least one polymerizable calix[n]arene according to formula (I),
(b) 0.01 to 5% by weight, preferably 0.01 to 2% by weight, particularly preferably 0.01 to 1.5% by weight, of initiator,
(c) 1 to 30% by weight, preferably 5 to 20% by weight, particularly preferably 5 to 15% by weight, of at least one additional monomer which can polymerize under cationic and/or radical conditions and/or at least one additional monomer which can polymerize by ring opening, particularly preferably a polyfunctional (meth)acrylate,
(d) 5 to 85% by weight, particularly preferably 10 to 80% by weight, of filler and
(e) 0.01 to 5% by weight, preferably 0.01 to 3% by weight, particularly preferably 0.01 to 2% by weight, of additive,
the percentages each time adding up to 100%.

Coating materials according to the invention preferably comprise:
(a) 1 to 70% by weight, particularly preferably 1 to 50% by weight, of at least one polymerizable calix[n]arene according to formula (I),
(b) 0.01 to 5% by weight, preferably 0.01 to 2% by weight, particularly preferably 0.1 to 1.5% by weight, of initiator,
(c) 5 to 70% by weight, preferably 5 to 60% by weight, particularly preferably 5 to 50% by weight, of at least one additional monomer which can polymerize under cationic and/or radical conditions and/or at least one additional monomer which can polymerize by ring opening, particularly preferably at least one polyfunctional (meth)acrylate,
(d) 1 to 30% by weight, preferably 3 to 20% by weight, particularly preferably 3 to 15% by weight, of a filler, preferably a nanoparticulate filler,
(e) 0.01 to 5% by weight, preferably 0.01 to 3% by weight, particularly preferably 0.01 to 2% by weight, very particularly preferably 0.01 to 1% by weight, of additive and
(f) 0 to 70% by weight, particularly preferably 0 to 30% by weight, of solvent,
the percentages each time adding up to 100%.

Dental adhesives according to the invention preferably comprise:
(a) 0.5 to 50% by weight, particularly preferably 1.0 to 30% by weight, of at least one polymerizable calix[n]arene according to formula (I),
(b) 0.01 to 5% by weight, particularly preferably 0.01 to 2% by weight, of at least one initiator,
(c) 5 to 70% by weight, particularly preferably 5 to 60% by weight, of at least one additional monomer which can polymerize under cationic and/or radical conditions and/or at least one monomer which can polymerize by ring opening, particularly preferably at least one polyfunctional (meth)acrylate,
(d) 0 to 30% by weight, particularly preferably 3 to 20% by weight, of a filler,
(e) 0.01 to 5% by weight, particularly preferably 0.01 to 3% by weight, of additives and
(f) 0 to 50% by weight, particularly preferably 0 to 20% by weight, of solvent,
the percentages adding up to 100%.

The invention is more fully explained below with the help of examples.

Example 1

Synthesis of a Calix[6]Arene Tetramethacrylate V-9

$R^1$ to $R^6$=random mixture of

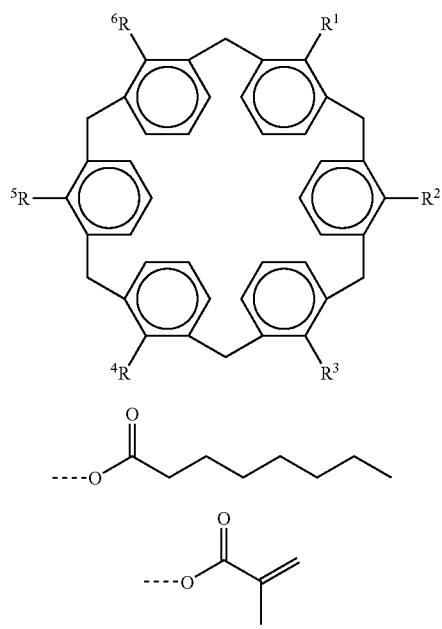

9.6 g (15 mmol) of hexahydroxycalix[6]arene and 5.2 g (130 mmol) of 60% NaH in silicone oil are added to 80 ml of dry dimethylformamide in a 250 ml flask with a nitrogen stopcock and stirred for 5 hours at AT. Subsequently, 5.2 ml (30 mmol) of octanoyl chloride are slowly added to the suspension and stirred at AT for an additional 36 h. Subsequently, 5.8 ml (60 mmol) of methacryloyl chloride are slowly added and stirred for a further 72 h. The darkly coloured suspension is added to 600 ml of water, resulting in the precipitation of a white solid. This is filtered off and copiously washed with water. The product is recrystallized from toluene and ethanol. The yield of product V-9 is 8.1 g. The MALDI-TOF analysis of the product gave a substitution pattern of 2 octanoic acid groups and 2-4 methacrylate groups.

Example 2

Synthesis of a Calix[6]Arene Dodecamethacrylate V-15

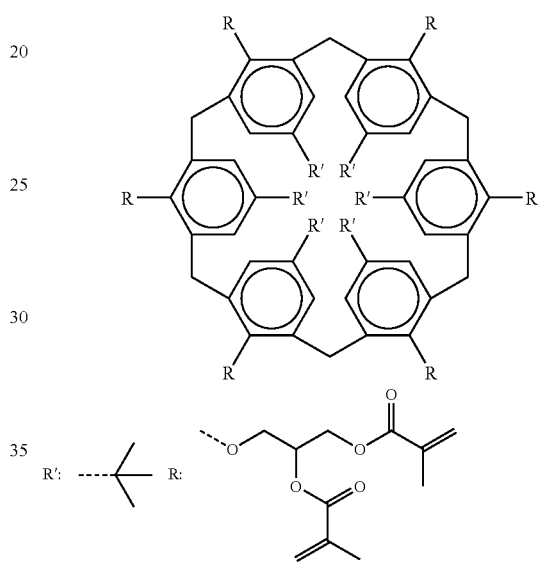

0.98 g of p-tert-butylcalix[6]arene (1 mmol), 0.16 g of tert-butylammonium bromide (TBAB) (1.8 mmol) and a spatula tip of phenothiazine are mixed with 15 ml of N-methylpyrrolidone (NMP) and added to a 50 ml round-bottomed flask. Subsequently, 4.3 g of glycidyl methacrylate (GMA) (30 mmol) are added to the solution. The charge is stirred at a temperature of 120° C. at a power of at most 100 watts for 300 min in the microwave field. The clear brown solution obtained is precipitated from 500 ml of water, filtration is carried out and finally drying is carried out under high vacuum. The yield of product is 1.5 g. The MALDI-TOF analysis of the product gave a mixture of products of the 1-6-fold reaction of p-tert-butylcalix[6]arene with GMA.

6 g of this calix[6]arene derivative are dissolved in 100 ml of $CH_2Cl_2$, mixed with 2.5 g of triethylamine (25 mmol) and stirred for 20 minutes. 3.1 g of methacryloyl chloride (30 mmol), dissolved in 50 ml of $CH_2Cl_2$, are added dropwise to the solution in 2 hours at ambient temperature under nitrogen. Subsequently, the reaction mixture is stirred for a further 4 days. The organic phase is then washed twice with each time 150 ml of saturated $NaHCO_3$ solution and, finally, with 400 ml of $H_2O$. The organic phase is dried with $Na_2SO_4$ and the solvent is removed. The yield of product V-15 is 8.5 g.

Example 3

Synthesis of p-Propyloxycalix[4]Arenenitrone V-10

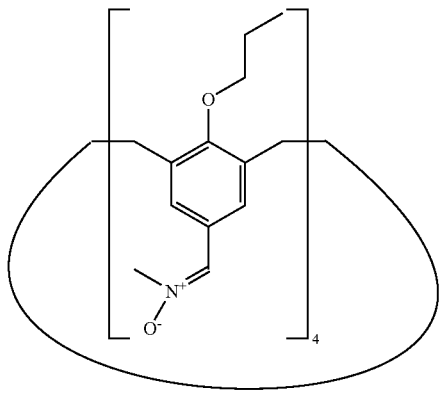

5,11,17,23-Tetraformyl-25,26,27,28-tetrapropoxycalix[4]arene (4.5 mmol) and N-methylhydroxylamine hydrochloride (27 mmol) are suspended in 60 ml of ethanolic NaOH (27 mmol) solution and stirred at ambient temperature under an $N_2$ atmosphere. After complete reaction has been achieved (FTIR), the reaction is brought to an end. Subsequently, the solvent is removed on a rotary evaporator. The crude product is extracted by shaking with water/chloroform (each 100 ml). The cloudy organic phase is separated and filtered and, subsequently, the solvent is removed on a rotary evaporator. The product is dried under oil pump vacuum. Minimal amounts of impurity are separated by column chromatography with methanol. The yield of product V-10 is approximately 100%.

Example 4

Preparation of a Composite Cement Based on the Polymerizable Calix[6]Arene V-15 from Example 2

A composite fixing cement based on a methacrylate mixture (Material A, Comparison) and with incorporation of the calix[6]arene V-15 from Example 2 (Material B) was prepared in accordance with the Table 1 listed below using an "Exact" roller mill (Exakt Apparatebau, Norderstedt). Corresponding test specimens were prepared from the materials, which were exposed to a dental light source (Spectramat®, Ivoclar Vivadent AG) for 2 times 3 minutes and accordingly cured. The flexural strength and the flexural E-modulus were determined according to the ISO standard ISO-4049 (Dentistry—Polymer-based filling, restorative and luting materials).

TABLE 1

Composite cement composition (figures in % by weight)

| Substances | Material A | Material B |
|---|---|---|
| Triethylene glycol dimethacrylate | 39.6 | 31.8 |
| Calix[6]arene V-15 from Example 2 | — | 7.8 |
| Aerosil OX-50 (Degussa) | 41.3 | 41.3 |
| Ytterbium trifluoride (Rhône-Poulenc) | 18.7 | 18.7 |
| Photoinitiator[1] | 0.4 | 0.4 |

[1]Mixture of camphorquinone (0.24% by weight) and ethyl p-(N,N-dimethylamino)benzoate (0.26% by weight)

It is clear, from Table 2, that the material B, in comparison with the material A (based on a purely conventional methacrylate mixture), at least results in comparable mechanical properties.

TABLE 2

Cement properties

| Material property | Material A | Material B |
|---|---|---|
| Flexural strength (MPa) after 24 h | 77 | 58 |
| Flexural strength (MPa) after 24 h SW[1] | 71 | 62 |
| Flexural E-modulus (GPa) after 24 h | 4.32 | 4.20 |
| Flexural E-modulus (GPa) after 24 h SW | 4.10 | 4.00 |

[1]SW = storage of the test specimens under water at 37° C.

Example 5

Preparation of a Filling Composite Based on the Polymerizable Calix[6]Arene V-15 from Example 2

A filling composite based on a methacrylate mixture (Material C, Comparison) and with incorporation of the calix[6]arene V-15 from Example 2 (Material D) was prepared in accordance with the Table 3 listed below using an LPM 0.1 SP kneader (Linden, Marienheide). Test specimens were prepared and cured from the materials analogously to Example 3. The flexural strength, the flexural E-modulus and the polymerization shrinkage were determined according to the ISO standard ISO-4049.

TABLE 3

Filling composite composition (figures in % by weight)

| Substances | Material C | Material D |
|---|---|---|
| Tetric monomer[1] | 18.1 | 16.3 |
| Calix[6]arene V-15 from Example 2 | — | 1.8 |
| Glass filler GM27884 (Degussa)[2] | 52.2 | 52.2 |
| Sphärosil (Tokoyama Soda)[3] | 14.5 | 14.5 |
| Ytterbium trifluoride (Rhône-Poulenc) | 15.0 | 15.0 |
| Photoinitiator[4] | 0.2 | 0.2 |

[1]Mixture of 42.4% by weight of Bis-GMA, 37.4% by weight of UDMA and 20.2% by weight of triethylene glycol dimethacrylate,
[2]silanized Ba Al borosilicate glass filler with a mean particle size of 1.5 μm,
[3]$SiO_2/ZrO_2$ mixed oxide (mean primary particle size: 250 nm),
[4]mixture of camphorquinone (0.24% by weight) and ethyl p-(N,N-dimethylamino)benzoate (0.26% by weight)

TABLE 4

Filling composite properties

| Material property | Material C | Material D |
|---|---|---|
| Flexural strength (MPa) after 24 h | 140 | 121 |
| Flexural strength (MPa) after 24 h SW[1] | 163 | 150 |
| Flexural E-modulus (GPa) after 24 h | 11.4 | 11.2 |
| Flexural E-modulus (GPa) after 24 h SW | 11.8 | 10.9 |
| Polymerization shrinkage (Vol %) | −3.98 | −3.22 |

[1] SW = storage of the test specimens under water at 37° C.

It is clear, from Table 4, that the material D, in comparison with the material C (based on a purely conventional methacrylate mixture), results, with comparable mechanical properties, in a significantly reduced polymerization shrinkage.

Example 6

Preparation of a Filling Composite Based on the Polymerizable Calix[6]Arene V-9 from Example 1

A filling composite based on a methacrylate mixture (Material E, Comparison) and with incorporation of the calix[6]arene V-9 from Example 1 (Material F) was prepared with the components in Table 5 using a VPL 1.5 kneader (Grieser, Lampertheim). Test specimens conforming to standard specifications were prepared and cured from the materials. The flexural strength, the flexural E-modulus and the polymerization shrinkage or the polymerization shrinking stress were determined according to the ISO standard ISO-4049.

TABLE 5

Filling composite composition (figures in % by weight)

| Substances | Material E | Material F |
| --- | --- | --- |
| TEGDMA[1] | 9.1 | 7.8 |
| Bis-GMA | 9.1 | 9.1 |
| Calix[6]arene V-9 from Example 1 | — | 1.3 |
| Glass filler GM018-053 (Schott)[2] | 76.0 | 76.0 |
| Nano-SiO$_2$[3] | 5.0 | 5.0 |
| Stabilizers | 0.3 | 0.3 |
| Photoinitiator[4] | 0.5 | 0.5 |

[1] Triethylene glycol dimethacrylate,
[2] silanized Ba Al borosilicate glass filler with a mean particle size of 0.7 µm,
[3] SiO$_2$ dispersion (mean particle size: 20 nm),
[4] mixture of camphorquinone (0.36% by weight) and ethylhexyl p-(N,N-dimethylamino) benzoate (0.14% by weight)

TABLE 6

Filling composite properties

| Material property | Material E | Material F |
| --- | --- | --- |
| Flexural strength (MPa) after 24 h SW[1] | 116 | 103 |
| Flexural E-modulus (GPa) after 24 h SW | 7.8 | 7.9 |
| Polymerization shrinkage (Vol %) | −2.4 | −1.8 |
| Polymerization shrinking stress (MPa) after 24 h SW | 5.9 | 5.4 |

[1] SW = storage of the test specimens under water at 37° C.

It is clear, from Table 6, that the material F, in comparison with the material E (based on a purely conventional methacrylate mixture), results, with comparable mechanical properties, in a significantly reduced polymerization shrinkage.

Example 7

Preparation of a Filling Composite Based on the Crosslinkable Calix[6]Arene V-10 from Example 3

A filling composite based on a methacrylate mixture (Material E, Comparison) and with incorporation of the calix[4]arene V-10 from Example 3 (Material G) was prepared with the components in Table 6 using a VPL 1.5 kneader (Grieser, Lampertheim). Test specimens conforming to standard specifications were prepared and cured from the materials. The flexural strength, the flexural E-modulus and the polymerization shrinkage or the polymerization shrinking stress were determined according to the ISO standard ISO-4049.

TABLE 7

Filling composite composition (figures in % by weight)

| Substances | Material E | Material G |
| --- | --- | --- |
| TEGDMA[1] | 9.1 | 7.8 |
| Bis-GMA | 9.1 | 9.1 |
| Calix[4]arene V-10 from Example 3 | — | 1.3 |
| Glass filler GM018-053 (Schott)[2] | 76.0 | 76.0 |
| Nano-SiO$_2$[3] | 5.0 | 5.0 |
| Stabilizers | 0.3 | 0.3 |
| Photoinitiator[4] | 0.5 | 0.5 |

[1] Triethylene glycol dimethacrylate,
[2] silanized Ba Al borosilicate glass filler with a mean particle size of 0.7 µm,
[3] SiO$_2$ dispersion (mean particle size: 20 nm),
[4] mixture of camphorquinone (0.36% by weight) and ethylhexyl p-(N,N-dimethylamino) benzoate (0.14% by weight)

TABLE 8

Filling composite properties

| Material property | Material E | Material G |
| --- | --- | --- |
| Flexural strength (MPa) after 24 h SW[1] | 116 | 90 |
| Flexural E-modulus (GPa) after 24 h SW | 7.8 | 6.5 |
| Polymerization shrinkage (Vol %) | −2.4 | −1.7 |
| Polymerization shrinking stress (MPa) after 24 h SW | 5.9 | 4.6 |

[1] SW = storage of the test specimens under water at 37° C.

It is clear, from Table 8, that the material G, in comparison with the material E (based on a purely conventional methacrylate mixture), results, with slightly diminished mechanical properties, in a significantly reduced polymerization shrinkage.

While specific embodiments of the invention have been shown and described in detail to illustrate the inventive principles, it will be understood that the invention may be embodied otherwise without departing from such principles.

We claim:

1. A process for preparing dental materials comprising the step of mixing:
   (a) at least one polymerizable calix[n]arene according to general formula (I),

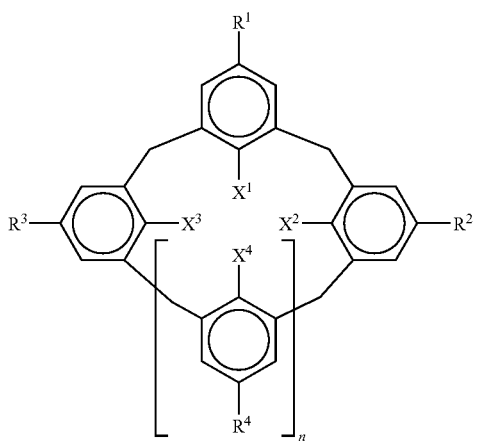

in which
n=1 to 5,
$R^1$-$R^4$=independently of one another, H, a $C_1$- to $C_{15}$-alkyl radical which can be interrupted by 0, a phenyl radical or a benzyl radical,
$X^1$ represents a group with the structure:
$Y^1$—$R_a^1$($Y_a^1$—$R_b^1$-$PG^1$)$_m$, in which
$Y^1$=not present or O, ester, amide or urethane,
$R_a^1$=an m-valent organic radical comprising from 1 to 30 carbon atoms and also from up to 6 heteroatoms,
m=1 to 3,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group
$X^2$-$X^4$=independently of one another, not present, OH or $C_1$- to $C_{10}$-alkyl radical and which can have, independently of one another, the same meaning of $X^1$ and, in addition, can represent a group with the structure: ($Y_a^2$—$R_b^2$-AG)$_p$, in which
$Y_a^2$=not present or O, ester, amide or urethane,
$R_b^2$=a p-valent organic radical comprising from 1 to 20 carbon atoms and also from up to 4 heteroatoms,
p=1 to 3 and
AG=an anchoring group, selected from —P=O(OH)$_2$, —O—P=O(OH)$_2$, —COOH or —O—SO$_2$OH,
  (b) initiator,
  (c) at least one additional monomer which polymerize under cationic and/or radical conditions and/or which polymerize by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,
  (d) filler, and
  (e) additive
wherein the percentages each time add up to 100%,
applying the mixture as cements on tooth,
wherein the percentage of cements being
  (a) 0.5 to 30% by weight of at least one calix[n]arene according to formula (I),
  (b) 0.01 to 2% by weight of initiator,
  (c) 1 to 30% by weight of at least one additional monomer which polymerize under cationic and/or radical, conditions and/or which polymerize by ring opening,
  (d) 5 to 70% by weight of filler and
  (e) 0.01 to 5% by weight of additive
the percentages each time add up to 100%.

2. A process according to claim 1, the dental materials comprising calix[n]arenes of the general formula (I):

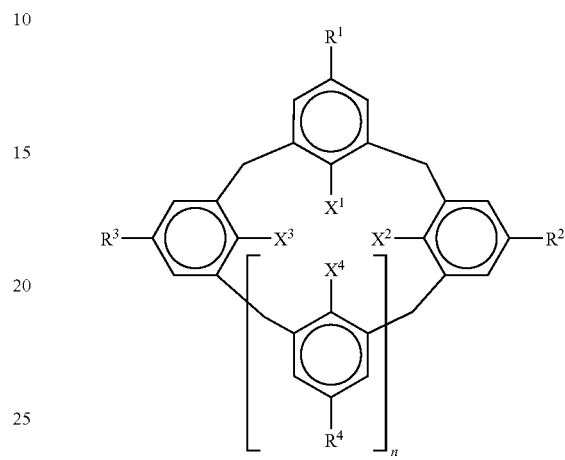

in which
n=1 to 3,
$R^1$-$R^4$=independently of one another, H, a $C_2$- to $C_{10}$-alkyl radical which can be interrupted by 0, a phenyl radical or a benzyl radical,
$X^1$ represents a group with the structure:
$Y^1$—$R_a^1$($Y_a^1$—$R_b^1$-$PG^1$)$_m$, in which
$Y^1$=not present or O, ester, amide or urethane,
$R_a^1$=an m-valent organic radical comprising from 1 to 15 carbon atoms and also from up to 3 heteroatoms,
m=1 to 2,
$Y_a^1$=not present or O, ester, amide or urethane,
$R_b^1$=not present or a $C_1$-$C_{26}$-alkylene radical which can be interrupted by oxygen atoms,
$PG^1$=a polymerizable group,
  and with furthermore
$X^2$-$X^4$=independently of one another, not present, OH or $C_1$- to $C_{10}$-alkyl radical and which can have, independently of one another, the same meaning of $X^1$ and, in addition, can represent a group with the structure: ($Y_a^2$—$R_b^2$-AG)$_p$, in which
$Y_a^2$=not present or O, ester, amide or urethane,
$R_b^2$=a p-valent organic radical comprising from 1 to 10 carbon atoms and also from up to 2 heteroatoms,
P=1 to 2 and
AG=an anchoring group, selected from —P=O(OH)$_2$, —O—P=O(OH)$_2$, —COOH or —O—SO$_2$OH.

3. A process according to claim 1, the dental materials comprising
  calix[n]arenes of the formula (I):

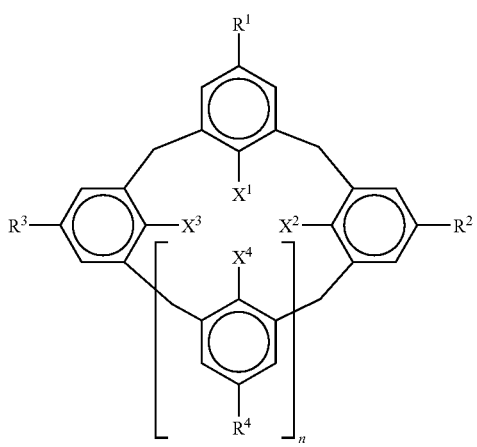

in which
n=1 to 3,
$R^1$-$R^4$=independently of one another, H, a $C_1$- to $C_{10}$-alkyl radical which can be interrupted by 0, or a benzyl radical,
$X^1$ represents a group with the structure:
$Y^1$—$R_a^1$($Y_a^1$—$R_b^1$-$PG^1$)$_m$, in which
$Y^1$=not present or O or ester,
$R_a^1$=an m-valent organic radical comprising from 1 to 15 carbon atoms and also from up to 3 oxygen atoms,
m=1 to 2,
$Y_a^1$=not present or O or ester,
$R_b^1$=not present or a $C_1$-$C_{26}$-alkylene radical which can be interrupted by oxygen atoms,
$PG^1$=a polymerizable group, a group, which polymerize under radical conditions, a cyclic group which polymerize under radical conditions by ring opening, the groups

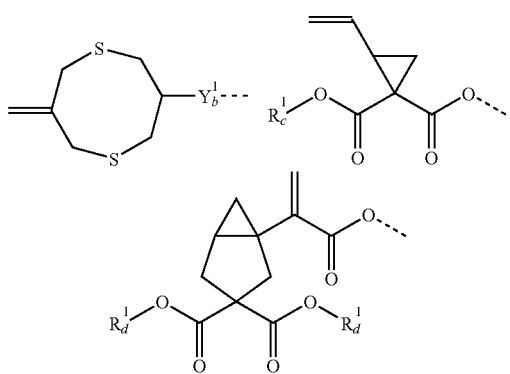

or a group which polymerize under cationic conditions, a cycloaliphatic epoxide or oxetane group or a polyreactive nitrone group,
with
$Y_b^1$=not present or O, ester or urethane,
$R_c^1$, $R_d^1$=independently of one another, $C_1$- to $C_5$-alkyl radical, a phenyl radical or a benzyl radical;
and with furthermore
$X^2$-$X^4$=independently of one another, not present or $C_1$- to $C_{10}$-alkyl radical and which can have, independently of one another, the same meaning of $X^1$ and, in addition, can represent a group with the structure: ($Y_a^2$—$R_b^2$-AG)$_p$, in which
$Y_a^2$=not present or O or ester, $R_b^2$=a p-valent organic radical comprising from 1 to 10 carbon atoms and also from up to 2 oxygen atoms,
p=1 to 2 and
AG=an anchoring group, selected from —P=O(OH)$_2$, —O—P=O(OH)$_2$, —COOH or —O—SO$_2$OH.

4. A process according to claim 1, the dental materials comprising,
(a) 0.5 to 20% by weight of at least one calix[n]arene according to formula (I),
(b) 0.01 to 1.5% by weight of initiator,
(c) 5 to 20% by weight of at least one additional monomer which polymerize under radical conditions and/or at least one additional monomer which polymerize by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,
(d) 10 to 60% by weight of filler and
(e) 0.01 to 3% by weight of additive,
the percentages each time adding up to 100%.

5. A process for preparing dental materials comprising the step of mixing:
(a) at least one polymerizable calix[n]arene according to general formula (I),

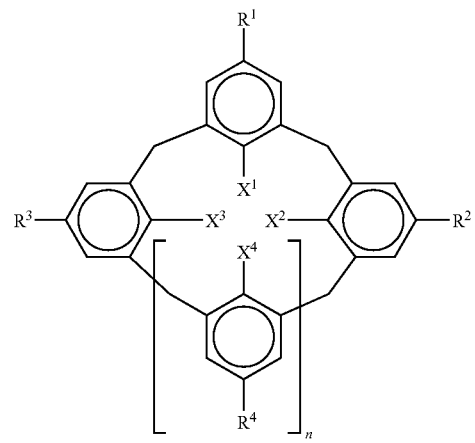

in which
n=1 to 5,
$R^1$-$R^4$=independently of one another, H, a $C_1$- to $C_{15}$-alkyl radical which can be interrupted by 0, a phenyl radical or a benzyl radical,
$X^1$ represents a group with the structure:
$Y^1$—$R_a^1$($Y_a^1$—$R_b^1$-$PG^1$)$_m$, in which
$Y^1$=not present or O, ester, amide or urethane,
$R_a^1$=an m-valent organic radical comprising from 1 to 30 carbon atoms and also from up to 6 heteroatoms,
m=1 to 3,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group
$X^2$-$X^4$=independently of one another, not present, OH or $C_1$- to $C_{10}$-alkyl radical and which can have, independently of one another, the same meaning of $X^1$ and, in addition, can represent a group with the structure: ($Y_a^2$—$R_b^2$-AG)$_p$, in which
$Y_a^2$=not present or O, ester, amide or urethane,
$R_b^2$=a p-valent organic radical comprising from 1 to 20 carbon atoms and also from up to 4 heteroatoms,
p=1 to 3 and AG=an anchoring group, selected from —P=O(OH)$_2$, —O—P=O(OH)$_2$, —COOH or —O—SO$_2$OH,
(b) initiator,
(c) at least one additional monomer which polymerize under cationic and/or radical conditions and/or which polymerize by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,
(d) filler,
(e) additive and
(f) optionally solvent
wherein the percentages each time add up to 100%,
applying the mixture as filling composites on tooth, the percentage of filling composites being
a) 0.5 to 70% by weight of at least one calix[n]arene according to formula (I),
(b) 0.01 to 5% by weight of initiator,
(c) 5 to 60% by weight of at least one additional monomer which can polymerize under ionic and/or radical conditions and/or at least one additional monomer which can polymerize by ring opening,
(d) 3 to 30% by weight of filler,
(e) 0.01 to 5% by weight of additive and
(f) 0 to 70% by weight of solvent,
the percentages each time add up to 100%.

6. A process according to claim 5, the dental materials comprising calix[n]arenes of the general formula (I):

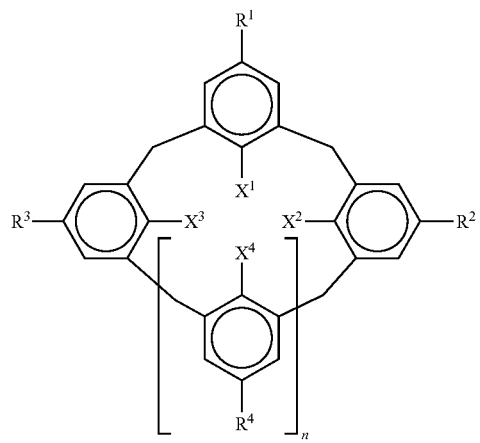

in which
n=1 to 3,
$R^1$-$R^4$=independently of one another, H, a $C_3$- to $C_{10}$-alkyl radical which can be interrupted by 0, a phenyl radical or a benzyl radical,
$X^1$ represents a group with the structure:
$Y^1$—$R_a^1$($Y_a^1$—$R_b^1$-$PG^1$)$_m$, in which
$Y^1$=not present or O, ester, amide or urethane,
$R_a^1$=an m-valent organic radical comprising from 1 to 15 carbon atoms and also from up to 3 heteroatoms,
m=1 to 2,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group,
and with furthermore
$X^2$-$X^4$=independently of one another, not present, OH or $C_1$- to $C_{10}$-alkyl radical and which can have, independently of one another, the same meaning of $X^1$ and, in addition, can represent a group with the structure: $(Y_a^2$—$R_b^2$-AG)$_p$, in which
$Y_a^2$=not present or O, ester, amide or urethane,
$R_b^2$=a p-valent organic radical comprising from 1 to 10 carbon atoms and also from up to 2 heteroatoms,
P=1 to 2 and
AG=an anchoring group, selected from —P=O(OH)$_2$, —O—P=O(OH)$_2$, —COOH or —O—SO$_2$OH.

7. A process according to claim 5, the dental materials comprising calix[n]arenes of the formula (I):

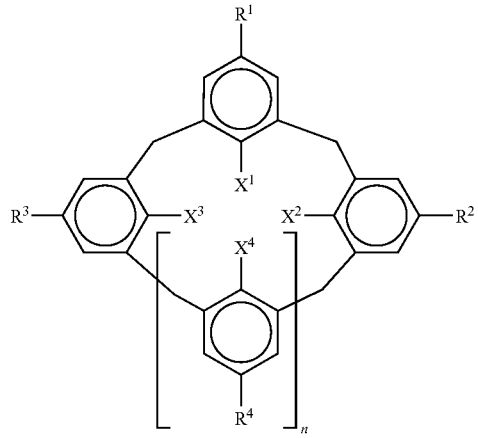

in which
n=1 to 3,
$R^1$-$R^4$=independently of one another, H, a $C_1$- to $C_{10}$-alkyl radical which can be interrupted by O, or a benzyl radical,
$X^1$ represents a group with the structure:
$Y^1$—$R_a^1$($Y_a^1$—$R_b^1$-$PG^1$)$_m$, in which
$Y^1$=not present or O or ester,
$R_a^1$=an m-valent organic radical comprising from 1 to 15 carbon atoms and also from up to 3 oxygen atoms,
m=1 to 2,
$Y_a^1$=not present or O or ester,
$R_b^1$=not present or a $C_1$-$C_{16}$-alkylene radical which can be interrupted by oxygen atoms,
$PG^1$=a polymerizable group, a group, which polymerize under radical conditions, a cyclic group which polymerize under radical conditions by ring opening, the groups

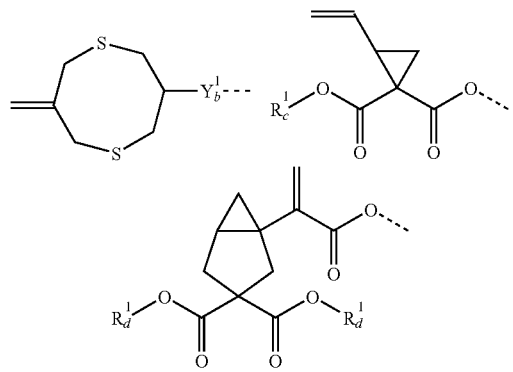

or a group which polymerize under cationic conditions, a cycloaliphatic epoxide or oxetane group or a polyreactive nitrone group, with
$Y_b^1$=not present or O, ester or urethane,
$R_c^1$, $R_d^1$=independently of one another, $C_1$- to $C_5$-alkyl radical, a phenyl radical or a benzyl radical;
and with furthermore
$X^2$-$X^4$=independently of one another, not present or $C_1$- to $C_{10}$-alkyl radical and which can have, independently of one another, the same meaning of $X^1$ and, in addition, can represent a group with the structure: $(Y_a^2—R_b^2-AG)_p$, in which
$Y_a^2$=not present or O or ester,
$R_b^2$=a p-valent organic radical comprising from 1 to 10 carbon atoms and also from up to 2 oxygen atoms,
p=1 to 2 and
AG=an anchoring group, selected from —P=O(OH)$_2$, —O—P=O(OH)$_2$, —COOH or —O—SO$_2$OH.

8. A process according to claim 5, the dental materials comprising,
(a) 0.5 to 20% by weight of at least one calix[n]arene according to formula (I),
(b) 0.01 to 2% by weight of initiator,
(c) 5 to 0.20% by weight of at least one additional monomer which polymerize under radical conditions and/or at least one additional monomer which polymerize by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,
(d) 10 to 80% by weight of filler and
(e) 0.01 to 3% by weight of additive,
the percentages each time adding up to 100%.

9. A process for preparing dental materials comprising the step of mixing:
(a) at least one polymerizable calix[n]arene according to general formula (I),

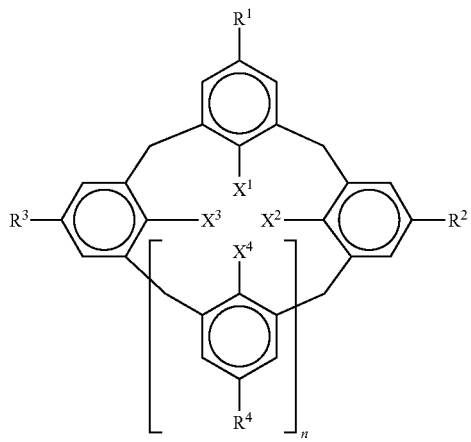

in which
n=1 to 5,
$R^1$-$R^4$=independently of one another, H, a $C_1$- to $C_{15}$-alkyl radical which can be interrupted by O, a phenyl radical or a benzyl radical,
$X^1$ represents a group with the structure:
$Y^1—R_a^1(Y_a^1—R_b^1-PG^1)_m$, in which
$Y^1$=not present or O, ester, amide or urethane,
$R_a^1$=an m-valent organic radical comprising from 1 to 30 carbon atoms and also from up to 6 heteroatoms,
m=1 to 3,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group
$X^2$-$X^4$=independently of one another, not present, OH or $C_1$- to $C_{10}$-alkyl radical and which can have, independently of one another, the same meaning of $X^1$ and, in addition, can represent a group with the structure: $(Y_a^2—R_b^2-AG)_p$, in which
$Y_a^2$=not present or O, ester, amide or urethane,
$R_b^2$=a p-valent organic radical comprising from 1 to 20 carbon atoms and also from up to 4 heteroatoms,
p=1 to 3 and
AG=an anchoring group, selected from —P=O(OH)$_2$, —O—P=O(OH)$_2$, —COOH or —O—SO$_2$OH,
(b) initiator,
(c) at least one additional monomer which polymerize under cationic and/or radical conditions and/or which polymerize by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,
(d) filler,
(e) additive and
(f) optionally solvent
wherein the percentages each time add up to 100%,
applying the mixture as coating materials on tooth, the percentage of coating materials being
(a) 0.5 to 70% by weight of at least one calix[n]arene according to formula (I),
(b) 0.01 to 5% by weight of initiator,
(c) 5 to 70% by weight of at least one additional monomer which can polymerize under ionic or radical conditions and/or at least one additional monomer which can polymerize by ring opening,
(d) 3 to 30% by weight of a filler,
(e) 0.01 to 5% by weight of additive and
(f) 0 to 50% by weight of solvent,
the percentages each time adding up to 100%.

10. A process according to claim 9, the dental materials comprising calix[n]arenes of the general formula (I):

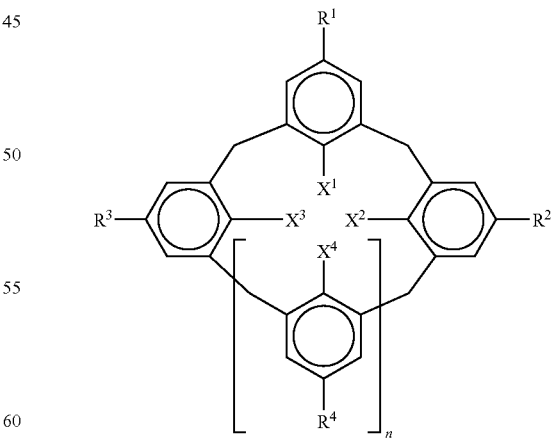

in which
n=1 to 3,
$R^1$-$R^4$=independently of one another, H, a $C_1$- to $C_{10}$-alkyl radical which can be interrupted by O, a phenyl radical or a benzyl radical, $X^1$ represents a group with the structure:
$Y^1$—$R_a^1(Y_a^1$—$R_b^1$-$PG^1)_m$, in which
$Y^1$=not present or O, ester, amide or urethane,
$R_a^1$=an m-valent organic radical comprising from 1 to 15 carbon atoms and also from up to 3 heteroatoms,
m=1 to 2,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group,
and with furthermore
$X^2$-$X^4$=independently of one another, not present, OH or $C_1$- to $C_{10}$-alkyl radical and which can have, independently of one another, the same meaning of $X^1$ and, in addition, can represent a group with the structure: $(Y_a^2$—$R_b^2$-$AG)_p$, in which
$Y_a^2$=not present or O, ester, amide or urethane,
$R_b^2$=a p-valent organic radical comprising from 1 to 10 carbon atoms and also from up to 2 heteroatoms,
P=1 to 2 and
AG=an anchoring group, selected from —P=O(OH)$_2$, —O—P=O(OH)$_2$, —COOH or —O—SO$_2$OH.

11. A process according to claim 9, the dental materials comprising
calix[n]arenes of the formula (I):

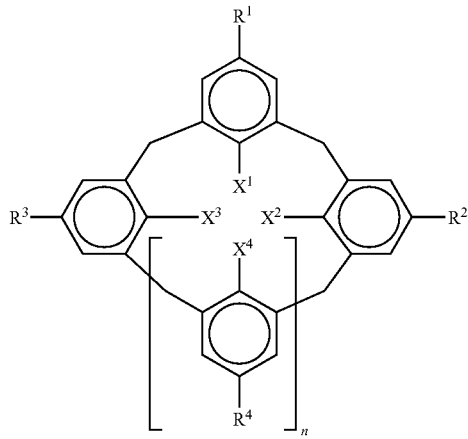

in which
n=1 to 3,
$R^1$-$R^4$=independently of one another, H, a $C_1$- to $C_{10}$-alkyl radical which can be interrupted by O, or a benzyl radical,
$X^1$ represents a group with the structure:
$Y^1$—$R_a^1(Y_a^1$—$R_b^1$-$PG^1)_m$, in which
$Y^1$=not present or O or ester,
$R_a^1$=an m-valent organic radical comprising from 1 to 15 carbon atoms and also from up to 3 oxygen atoms,
m=1 to 2,
$Y_a^1$=not present or O or ester,
$R_b^1$=not present or a $C_1$-$C_{16}$-alkylene radical which can be interrupted by oxygen atoms,
$PG^1$=a polymerizable group, a group, which polymerize under radical conditions, a cyclic group which polymerize under radical conditions by ring opening, the groups

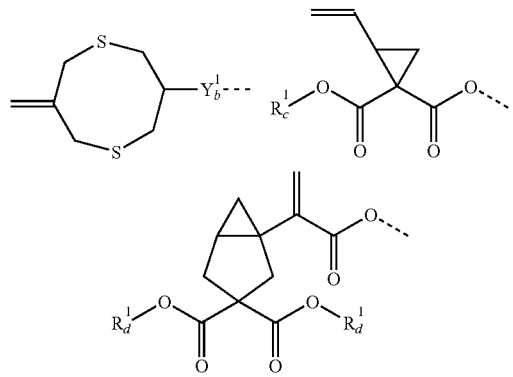

or a group which polymerize under cationic conditions, a cycloaliphatic epoxide or oxetane group or a polyreactive nitrone group,
with
$Y_b^1$=not present or O, ester or urethane,
$R_c^1$, $R_d^1$=independently of one another, $C_3$- to $C_5$-alkyl radical, a phenyl radical or a benzyl radical;
and with furthermore
$X^2$-$X^4$=independently of one another, not present or $C_1$- to $C_{10}$-alkyl radical and which can have, independently of one another, the same meaning of $X^1$ and, in addition, can represent a group with the structure: $(Y_a^2$—$R_b^2$-$AG)_p$, in which
$Y_a^2$=not present or O or ester,
$R_b^2$=a p-valent organic radical comprising from 1 to 10 carbon atoms and also from up to 2 oxygen atoms,
p=1 to 2 and
AG=an anchoring group, selected from —P=O(OH)$_2$, —O—P=O(OH)$_2$, —COOH or —O—SO$_2$OH.

12. A process according to claim 9, the dental materials comprising
(a) 1 to 50% by weight of at least one calix[n]arene according to formula (I),
(b) 0.01 to 1.5% by weight of initiator,
(c) 5 to 60% by weight of at least one additional monomer which polymerize under radical conditions and/or at least one additional monomer which polymerize by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,
(d) 3 to 20% by weight of a filler,
(e) 0.01 to 3% by weight of additive and
(f) 0 to 30% by weight of solvent,
the percentages each time adding up to 100%.

13. A process for preparing dental materials comprising the step of mixing:
(a) at least one polymerizable calix[n]arene according to general formula (I),

27

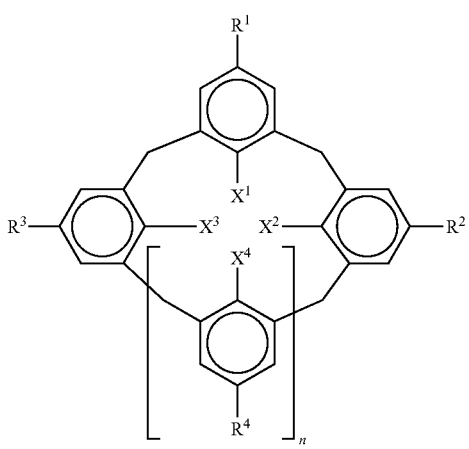

in which
n=1 to 5,
$R^1$-$R^4$=independently of one another, H, a $C_1$- to $C_{15}$-alkyl radical which can be interrupted by O, a phenyl radical or a benzyl radical,
$X^1$ represents a group with the structure:
$Y^1$—$R_a^1$($Y_a^1$—$R_b^1$-$PG^1$)$_m$, in which
$Y^1$=not present or O, ester, amide or urethane,
$R_a^1$=an m-valent organic radical comprising from 1 to 30 carbon atoms and also from up to 6 heteroatoms,
m=1 to 3,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group
$X^2$-$X^4$=independently of one another, not present, OH or $C_1$- to $C_{10}$-alkyl radical and which can have, independently of one another, the same meaning of $X^1$ and, in addition, can represent a group with the structure: ($Y_a^2$—$R_b^2$-AG)$_p$, in which
$Y_a^2$=not present or O, ester, amide or urethane,
$R_b^2$=a p-valent organic radical comprising from 1 to 20 carbon atoms and also from up to 4 heteroatoms,
p=1 to 3 and
AG=an anchoring group, selected from —P=O(OH)$_2$, —O—P=O(OH)$_2$, —COOH or —O—SO$_2$OH,
  (b) initiator,
  (c) at least one additional monomer which polymerize under cationic and/or radical conditions and/or which polymerize by ring opening,
  (d) filler,
  (e) additive and
  (f) optionally solvent
wherein the percentages each time add up to 100%,
applying the mixture as dental adhesives on tooth, the percentage of dental adhesives being
  (a) 0.5 to 70% by weight of at least one calix[n]arene according to formula (I),
  (b) 0.01 to 5% by weight of initiator,
  (c) 5 to 70% by weight of at least one additional monomer which can polymerize under radical conditions and/or at least one additional monomer which can polymerize by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,

28

(d) 3 to 30% by weight of filler,
  (e) 0.01 to 5% by weight of additives and
  (f) 0 to 50% by weight of solvent,
  the percentages each time add up to 100%.
14. A process according to claim 13, the dental materials comprising calix[n]arenes of the general formula (I):

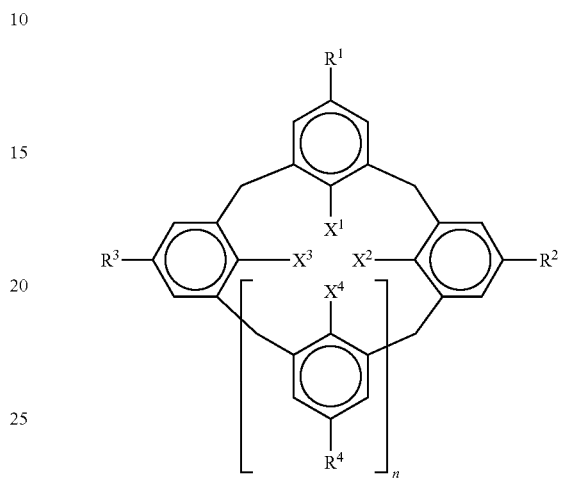

in which
n=1 to 3,
$R^1$-$R^4$=independently of one another, H, a $C_1$- to $C_{10}$-alkyl radical which can be interrupted by O, a phenyl radical or a benzyl radical,
$X^1$ represents a group with the structure:
  $Y^1$—$R_a^1$($Y_a^1$—$R_b^1$-$PG^1$)$_m$, in which
$Y^1$=not present or O, ester, amide or urethane,
$R_a^1$=an m-valent organic radical comprising from 1 to 15 carbon atoms and also from up to 3 heteroatoms,
m=1 to 2,
$Y_a^1$=not present or O, ester, amide or urethane,
$R_b^1$=not present or a $C_1$-$C_{16}$-alkylene radical which can be interrupted by oxygen atoms,
$PG^1$=a polymerizable group,
  and with furthermore
$X^2$-$X^4$=independently of one another, not present, OH or $C_1$- to $C_{10}$-alkyl radical and which can have, independently of one another, the same meaning of $X^1$ and, in addition, can represent a group with the structure: ($Y_a^2$—$R_b^2$-AG)$_p$, in which
$Y_a^2$=not present or O, ester, amide or urethane,
$R_b^2$=a p-valent organic radical comprising from 1 to 10 carbon atoms and also from up to 2 heteroatoms,
P=1 to 2 and
AG=an anchoring group, selected from —P=O(OH)$_2$, —O—P=O(OH)$_2$, —COOH or —O—SO$_2$OH.
15. A process according to claim 13, the dental materials comprising
  calix[n]arenes of the formula (I):

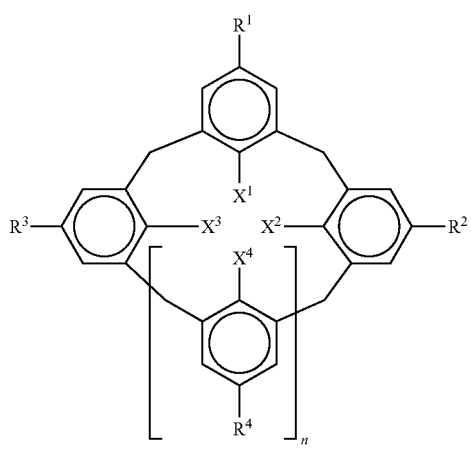

in which
n=1 to 3,
$R^1$-$R^4$=independently of one another, H, a $C_1$- to $C_{10}$-alkyl radical which can be interrupted by O, or a benzyl radical,
$X^1$ represents a group with the structure:
$Y^1$—$R_a^1$($Y_a^1$—$R_b^1$-$PG^1$)$_m$, in which
$Y^1$=not present or O or ester,
$R_a^1$=an m-valent organic radical comprising from 1 to 15 carbon atoms and also from up to 3 oxygen atoms,
m=1 to 2,
$Y_a^1$=not present or O or ester,
$R_b^1$=nor present or a $C_1$-$C_{16}$-alkylene radical which can be interrupted by oxygen atoms,
$PG^1$=a polymerizable group, a group, which polymerize under radical conditions, a cyclic group which polymerize under radical conditions by ring opening, the groups

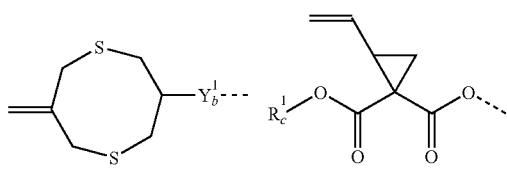

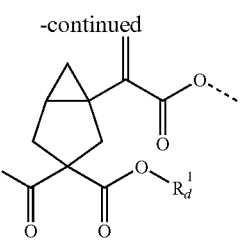

or a group which polymerize under cationic conditions, a cycloaliphatic epoxide or oxetane group or a polyreactive nitrone group,
with
$Y_b^1$=not present or O, ester or urethane,
$R_c^1$, $R_d^1$=independently of one another, $C_1$- to $C_5$-alkyl radical, a phenyl radical or a benzyl radical;
and with furthermore
$X^2$-$X^4$=independently of one another, not present or $C_1$- to $C_{10}$-alkyl radical and which can have, independently of one another, the same meaning of $X^1$ and, in addition, can represent a group with the structure: $(Y_a^2—R_b^2-AG)_p$, in which
$Y_a^2$=not present or O or ester,
$R_b^2$=a p-valent organic radical comprising from 1 to 10 carbon atoms and also from up to 2 oxygen atoms,
p=1 to 2 and
AG=an anchoring group, selected from —P=O(OH)$_2$, —O—P=O(OH)$_2$, —COOH or —O—SO$_2$OH.

16. A process according to claim 13, the dental materials comprising
(a) 1 to 30% by weight of a calix[n]arene according to formula (I),
(b) 0.01 to 2% by weight of at least one initiator,
(c) 5 to 60% by weight of at least one additional monomer which polymerize under cationic and/or radical conditions and/or by ring opening, the additional monomer comprising mono- or polyfunctional vinylcyclopropanes or bicyclic cyclopropaneacrylates or cyclic allyl sulphides, or polyfunctional (meth)acrylates or mixtures of these monomers,
(d) 3 to 20% by weight of filler,
(e) 0.01 to 3% by weight of additives and
(f) 0 to 20% by weight of solvent,
the percentages adding up to 100%.

* * * * *